US00PP16350P2

(12) United States Plant Patent
Herdegen

(10) Patent No.: US PP16,350 P2
(45) Date of Patent: Mar. 14, 2006

(54) ***SEDUM* PLANT NAMED 'GARBRO'**

(50) Latin Name: *Sedum telephium×Sedum spectabile*
Varietal Denomination: Garbro

(75) Inventor: Susanne Herdegen, Dexheim (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/045,977

(22) Filed: Jan. 28, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Sedum* plant named 'Garbro', characterized by its upright plant habit; freely branching growth habit; olive green-colored leaves; and red purple-colored flowers.

1 Drawing Sheet

Botanical designation: *Sedum telephium×Sedum spectabile.*
Cultivar denomination: 'Garbro'.

BACKGROUND OF THE INVENTION

The present Invention relates to a new and distinct cultivar of *Sedum* plant, botanically known as *Sedum telephium× Sedum spectabile,* and hereinafter referred to by the name 'Garbro'.

The new *Sedum* is a product of a planned breeding program conducted by the Inventor in Gensingen, Germany. The objective of the breeding program is to develop new compact *Sedum* cultivars with uniform growth habit and attractive flower coloration.

The new *Sedum* originated from a cross-pollination made by the Inventor during the summer of 2001 of the *Sedum telephium* cultivar Munstead Dark Red, not patented, as the female, or seed, parent with the *Sedum spectabile* cultivar Carmen, not patented, as the male, or pollen, parent. The new *Sedum* was discovered and selected by the Inventor as a single flowering plant within the progeny of the stated cross-pollination grown in a controlled environment in Gensingen, Germany during the summer of 2001.

Asexual reproduction of the new cultivar by terminal cuttings at Bonsall, Calif., since Jul. 1, 2000, has shown that the unique features of this new *Sedum* are stable and reproduced true to type in successive generations.

SUMMARY OF THE INVENTION

Plants of the cultivar Garbro have not been observed under all possible environmental conditions. The phenotype may vary somewhat with variations in environment such as temperature and light intensity without, however, any variance in genotype.

The following traits have been repeatedly observed and are determined to be the unique characteristics of 'Garbro'. These characteristics in combination distinguish 'Garbro' as a new and distinct cultivar:

1. Upright plant habit.
2. Freely branching growth habit.
3. Olive green-colored leaves.
4. Red purple-colored flowers.

Plants of the new *Sedum* can be compared to plants of the female parent, the cultivar Munstead Dark Red. Plants of the new *Sedum* differ from plants of the cultivar Munstead Dark Red in the following characteristics:

1. Plants of the new *Sedum* are more freely branching than plants of the cultivar Munstead Dark Red.
2. Plants of the new *Sedum* have lighter colored foliage than plants of the cultivar Munstead Dark Red.
3. Plants of the new *Sedum* have darker colored flowers than plants of the cultivar Munstead Dark Red.

Plants of the new *Sedum* can be compared to plants of the male parent, the cultivar Carmen. Plants of the new *Sedum* differ from plants of the cultivar Carmen in the following characteristics:

1. Plants of the new *Sedum* are more freely branching than plants of the cultivar Carmen.
2. Plants of the new *Sedum* have more freely branching inflorescences than plants of the cultivar Carmen.
3. Plants of the new *Sedum* and the cultivar Carmen differ in flower color as plants of the cultivar Carmen have pink-colored flowers.

Plants of the new *Sedum* can also be compared to plants of the *Sedum telephinum* cultivar Lajos, disclosed in U.S. Plant. Pat. No. 14,421. In side-by-side comparisons conducted in Bonsall, Calif., plants of the new *Sedum* differed from plants of the cultivar Lajos in the following characteristics:

1. Plants of the new *Sedum* were more compact than plants of the cultivar Lajos.
2. Plants of the new *Sedum* and the cultivar Lajos differed in leaf coloration as plants of the Lajos had variegated leaves.
3. Plants of the new *Sedum* and the cultivar Lajos differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Sedum*.

The photograph at the bottom of the sheet comprises a side perspective view of a typical flowering plant of 'Garbro' grown in a 10-cm container.

The photograph at the top of the sheet comprises a close-up view of a typical inflorescence of 'Garbro'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the summer in an outdoor nursery in Bonsall, Calif. for about twelve weeks in 10-cm containers. During the production of the plants, day temperatures ranged from 18 to 35° C. and night temperatures ranged from 10 to 21° C.

Botanical classification: *Sedum telephium*×*Sedum spectabile* cultivar Garbro.

Parentage:

*Female parent.*—*Sedum telephium* cultivar Munstead Dark Red, not patented.

*Male parent.*—*Sedum spectabile* cultivar Carmen, not patented.

Propagation:

*Type cutting.*—Terminal vegetative cuttings.

*Time to initiate roots, summer.*—About 14 days at 20° C.

*Time to initiate roots, winter.*—About 18 days at 20° C.

*Time to produce a rooted cutting.*—About 20 days at 20° C.

*Root description.*—Fine; white in color.

*Rooting habit.*—Freely branching.

Plant description:

*Form.*—Upright plant form. Freely branching, about eight or nine lateral branches per plant; vigorous growth habit. Numerous single flowers arranged in terminal and axillary panicles.

*Plant height.*—About 28 cm.

*Plant width.*—About 20 cm.

*Lateral branch description.*—Length: About 25 cm. Diameter: About 1.5 cm. Internode length: About 1.5 cm. Strength: Strong. Aspect: Mostly upright. Texture: Smooth, glabrous; succulent. Color: 187D.

*Foliage description.*—Arrangement: Alternate, simple; sessile. Length: About 8.8 cm. Width: About 2.2 cm. Shape: Elliptical to linear. Apex: Acute. Base: Attenuate; clasping. Margin: Irregularly serrate. Texture, upper and lower surfaces: Smooth, glabrous. Venation pattern: Pinnate; arcuate. Color: Developing foliage, upper and lower surfaces: 146A. Fully expanded foliage, upper surface: 147A; venation, 187C. Fully expanded foliage, lower surface: 147B; venation, 185B.

Flower description:

*Flower arrangement and shape.*—Small single star-shaped flowers arranged in terminal and axillary panicles; panicles roughly hemispherical. Flowers face mostly upright. Freely flowering, about 200 open flowers and flower buds per lateral branch.

*Natural flowering season.*—Flowering continuous from August through October in Southern California.

*Flower longevity on the plant.*—Individual last about two weeks on the plant. Flowers persistent.

*Flower buds.*—Length: About 6 mm. Diameter: About 3 mm. Shape: Ovoid. Color: 157A; towards the apex, 182C.

*Inflorescence diameter.*—About 10 cm.

*Inflorescence height.*—About 12.5 cm.

*Flowers.*—Diameter: About 8 mm. Depth (height): About 6 mm.

*Petals.*—Arrangement: Five, fused at base. Length: About 4 mm. Width: About 2 mm. Shape: Elliptic. Apex: Acuminate. Margin: Entire. Texture, upper and lower surfaces: Smooth, glabrous. Color: When opening and fully opened, upper surface: 186D. When opening and fully opened, lower surface: Towards the apex, 186C; towards the base, 157A.

*Calyx.*—Arrangement: Five sepals fused at the base; star-shaped. Length: About 2.5 mm. Diameter: About 3 mm. Sepal shape: Elliptic. Sepal apex: Acute. Sepal texture, upper and lower surfaces: Smooth, glabrous. Sepal color, upper and lower surfaces: 146A.

*Peduncles.*—Length, terminal panicles: About 2.3 cm. Length, axillary panicles: About 1.8 cm. Diameter, terminal panicles: About 4 mm. Diameter, axillary panicles: About 3 mm. Strength: Strong. Texture: Smooth, glabrous. Aspect, terminal panicles: Mostly erect. Aspect, axillary panicles: About 50 to 60° from the stem axis. Color: 183A.

*Pedicels.*—Length: About 6 mm. Diameter: About 1.5 mm. Strength: Strong. Texture: Smooth, glabrous. Aspect: About 45° from the stem axis. Color: 148A.

*Reproductive organs.*—Stamens: Quantity per flower/arrangement: Two; much reduced; situated at base of carpels. Anther shape: Rounded. Anther length: Less than 1 mm. Anther color: 10C. Pollen amount: Scarce. Pollen color: 10C. Pistils: Carpels: Five per flower; prominent; fused at the base; star-shaped. Carpel texture: Succulent. Carpel color: 183C to 183D. Stigma shape: Rounded; minute. Stigma color: 158A. Style length: About 1 mm. Style color: 183C. Ovary color: 183C to 183D; color becoming closer to 200B with development.

*Seed/fruit.*—Seed and fruit production has not been observed.

Disease/pest resistance: Plants of the new *Sedum* have not been noted to be resistant to pathogens and pests common to *Sedum*.

Weather tolerance: Plants of the new *Sedum* have exhibited good tolerance to rain and wind and have been observed to tolerate temperatures from −10 to 40° C.

It is claimed:

1. A new and distinct cultivar of *Sedum* plant named 'Garbro', as illustrated and described.

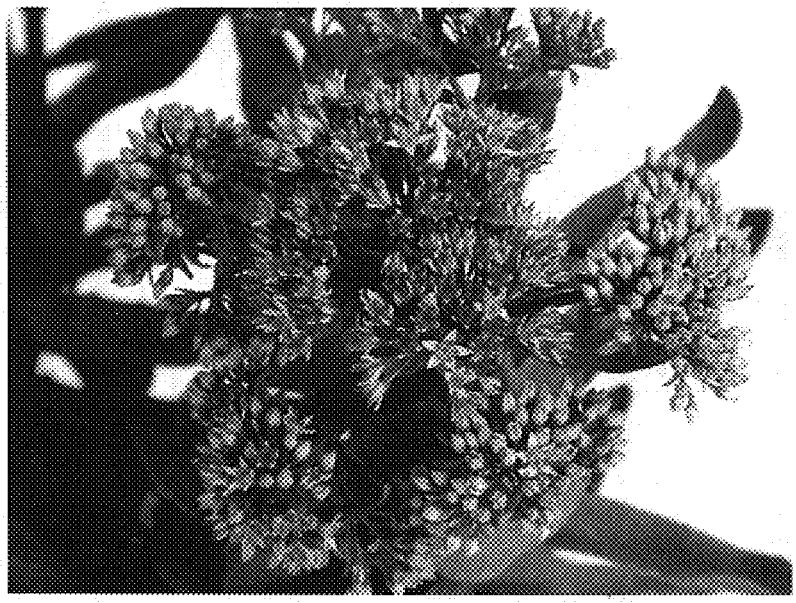
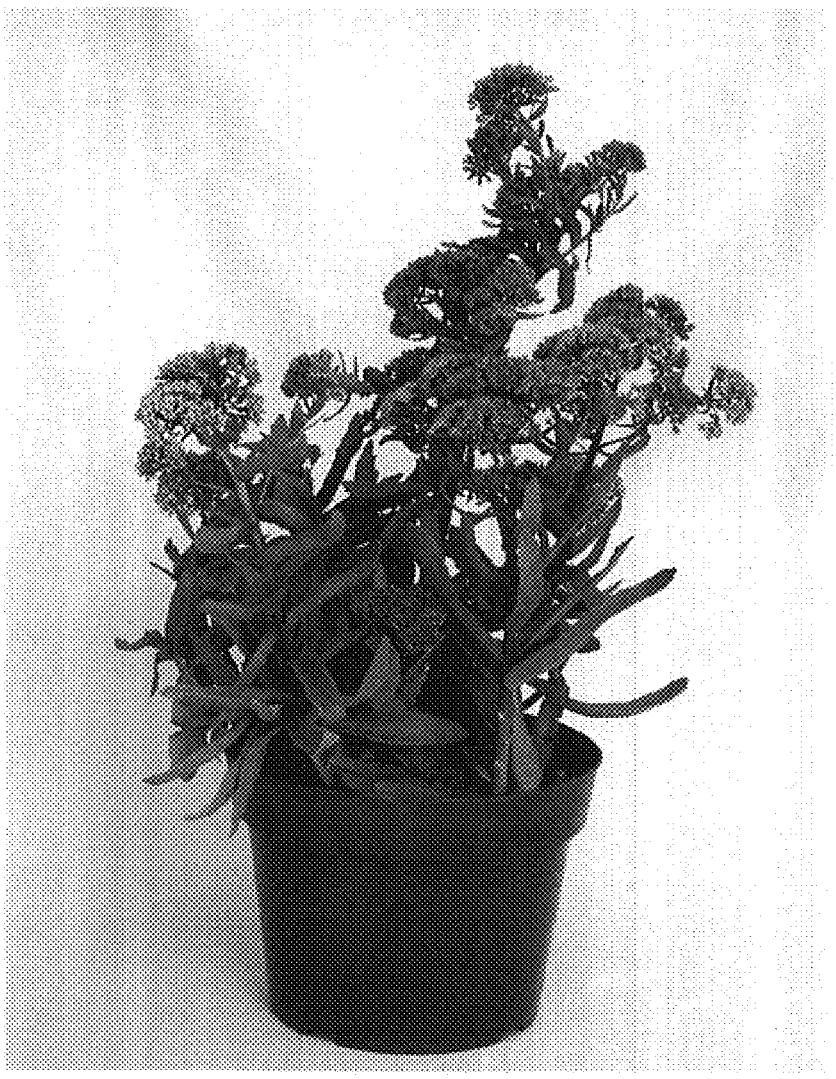

* * * * *